United States Patent [19]

Inamoto et al.

[11] 4,036,893
[45] July 19, 1977

[54] 8-EXO-HYDROXY-ENDO-TRICYCLO [5.2.2.0²,⁶]UNDECANE

[75] Inventors: Yoshiaki Inamoto; Yoshiaki Fujikura, both of Wakayama; Kiyoshi Tsuchihashi, Kainan; Naotake Takaishi, Iwade, all of Japan

[73] Assignee: Kao Soap Co., Ltd., Tokyo, Japan

[21] Appl. No.: 688,566

[22] Filed: May 21, 1976

[30] Foreign Application Priority Data

June 20, 1975 Japan .............................. 50-75293

[51] Int. Cl.² .............................................. C07C 35/22
[52] U.S. Cl. ................................... 260/617 F; 71/122; 252/522; 260/586 P; 260/586 G; 260/666 PY; 424/343
[58] Field of Search ..................................... 260/617 F

[56] References Cited

U.S. PATENT DOCUMENTS

| 2,394,583 | 2/1946 | Bruson ............................. 260/617 F |
| 2,404,787 | 7/1946 | Bruson ............................. 260/617 F |
| 2,875,244 | 2/1959 | Bartlett et al. ................... 260/617 F |
| 3,345,416 | 10/1967 | Tinsley et al. .................. 260/617 F |

OTHER PUBLICATIONS

Zwerfel et al, "Org. Reactions," vol. 13, pp. 1-20 (1963).

*Primary Examiner*—Norman Morgenstern
*Attorney, Agent, or Firm*—Blanchard, Flynn, Thiel, Boutell & Tanis

[57] ABSTRACT

The compound 8-exo-hydroxy-endo-tricyclo[5.2.2.0²,⁶]-undecane having the formula (I):

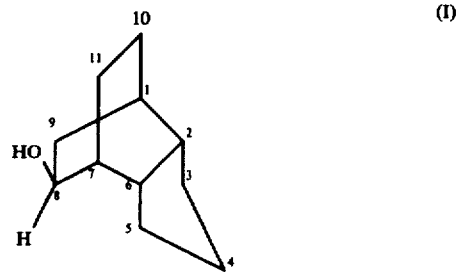

is prepared by subjecting endo-tricyclo[5.2.2.0²,⁶]undec-8-ene having the formula (II):

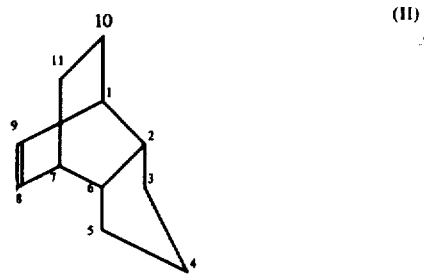

to hydroboration and oxidation with hydrogen peroxide.

1 Claim, No Drawings

8-EXO-HYDROXY-ENDO-TRICYCLO [5.2.2.0$^{2,6}$]UNDECANE

The present invention relates to a novel tricyclic undecanol having the formula (I):

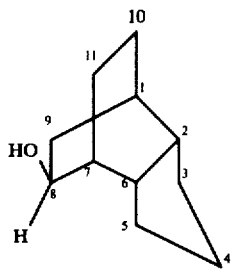

and a process for preparing same. More particularly, the invention relates to a process for preparing 8- exo-hydroxyendo-tricyclo[5.2.2.0$^{2,6}$]undecane having the formula (I) by subjecting endo-tricyclo [5.2.2.0$^{2,6}$]undec-8-ene having the formula (II):

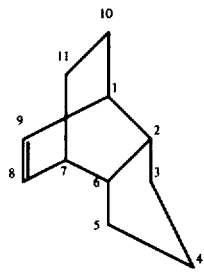

to hydroboration and oxidation with hydrogen peroxide.

The compound of formula (I) of the present invention is a novel substance. Because it has a polycyclic aliphatic structure like those of natural sesquiterpene alcohols and synthetic tricyclic aliphatic alcohols such as adamantyl alcohol, this compound will have substantially the physiological activities as those known compounds, such as an antiviral activity, an anti-fungal activity and a plant-growth stimulating activity and it will also be useful as an active odor-imparting ingredient of perfume compositions. Still further, as a great number of natural and synthetic aliphatic polycyclic compounds are incorporated as modifying groups into various pharmaceutical compounds and physiologically active compounds to improve the effects of those compounds, the compound of the present invention can be utilized similarly to those known compounds.

Aliphatic polycyclic compounds, for example, adamantane derivatives are distinguished from liner aliphatic compounds and from aromatic compounds in the features that they can be used as bases and as additives of lubricating oil compositions, fiber oiling compositions and components thereof, rust preventing compositions, extreme pressure additives and synthetic macromolecular monomers. In view of the polycyclic structure of the compound of the present invention, the compound of the present invention will also have these valuable properties. Accordingly, the compound of the present invention is valuable, per se, and as an intermediate and it can be used in various fields.

The fact that the unsaturated alcohol of formula (I) has the above-mentioned structure can be proved based on the following grounds.

It is known that hydroxyl groups of alcohols obtained by hydroboration of polycyclic olefins having, in general, an exo-arrangement [see, for example, G. Zweifel and H. C. Brown, Org. Reactions, 13, 1 (1963)]. It is explained that when diborane attacks the polycyclic olefin, it approaches the exo-side of a reduced steric hindrance (the so-called steric approach control). Therefore, in the hydroboration reaction of the process of the present invention, the hydroxy group of the product should be in the exo- configuration as shown by the formula (I). This can be further proved by the experimental fact that in the reaction represented by the reaction scheme given below, namely in the reaction of deriving a ketone (III) by subjecting the exo-alcohol (I) to Jones oxidation and reducing the ketone (III) with lithium aluminum hydride, the product alcohol (IV) is a substance different from the starting alcohol (I) and the hydroxyl group of this alcohol (IV) inevitably has a endo-arrangement:

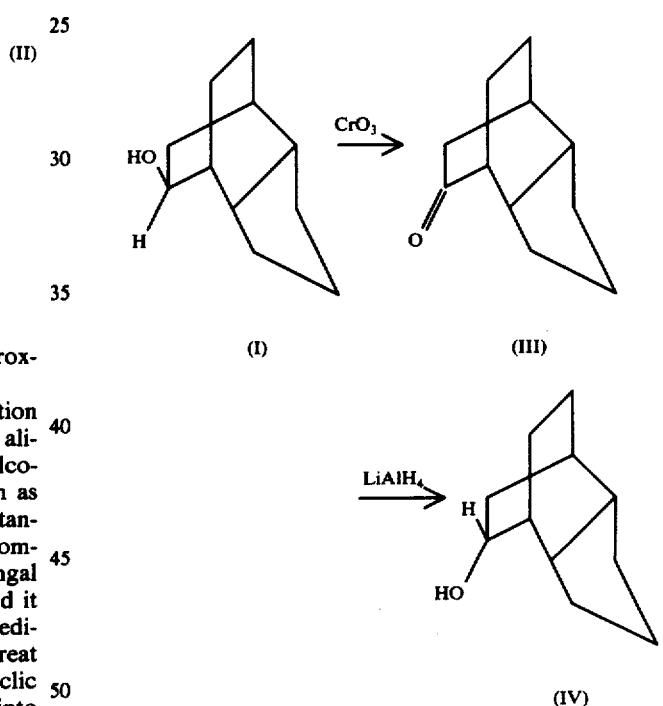

The reason is that it has been established that in the reduction of polycyclic ketones with a metal hydride complex, the reducing agent as well as the above-mentioned diborane undergoes the steric approach control and is allowed to approach only the exo-side and the hydroxyl group of the resulting alcohol has an endo-arrangement [see G. R. Wenzinger and J. A. Ors, J. Org. Chem., 39, 2060 (1974), P. E. Schueler and Y. E. Rhodes, ibid, 39, 2063 (1974) and H. C. Brown and W. J. Hammer, J. Amer. Chem. Soc., 89, 1524 (1967)]. If the hydroxy group of the compound (IV) has an endo-configuration, that of the isomer (I) should naturally have an exo-configuration. The fact that the arrangement correlation between products obtained by two independent steric selective reactions can be explained without contradiction indicates that the logic is correct.

In practicing the process of the present invention, customary reaction conditions (see, for example, G. Zweifel and H. C. Brown, the reference mentioned above) can be directly adopted for hydroboration and oxidation with hydrogen peroxide.

The starting substance used in the process of the present invention, endo-tricyclo [5.2.2.0$^{2,6}$]undec-8-ene (II) can be synthesized, for example, by the Diels-Alder reaction between 1,3-cyclohexadiene and cyclopentene as shown by the following reaction formula:

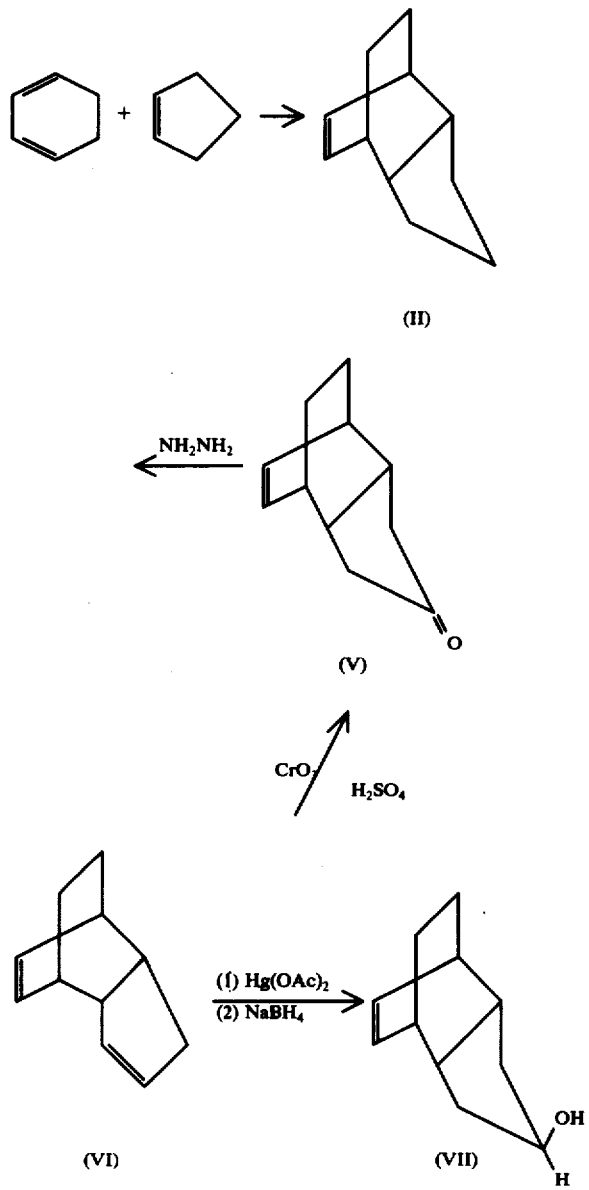

The compound of formula (II) is a novel trycycloundecene which has not heretofore been synthesized. In view of the fact that the compound (II) is in agreement with a substance (II) obtained by Wolff-Kishner reduction of endo-tricyclo-[5.2.2.0$^{2,6}$]undec-8-en-4-one (V), it is proved that the compound (II) is an endo-isomer as shown by the structural formula (II).

The unsaturated tricyclic ketone (V) can be synthesized by subjecting endo-tricyclo[5.2.2.0$^{2,6}$]undeca-3,8-diene (VI) to oxymercuration and reduction with sodium borohydride and subjecting the resulting 4-exo-hydroxy-endo-tricyclo-[5.2.2.0$^{2,6}$]undeca-8-ene (VIII) to Jones oxidation. The preparation of the compound of formula (VII) is disclosed in Japanese Ser. No. 62816/75, filed May 26, 1975, corresponding to U.S. Ser. No. 684,395, filed May 7, 1976.

There will now be described a preparation of the starting substance (II), an Example of the preparation of the formula (I) compound and an Example showing the antiviral activity of the formula (I) compound.

PREPARATION

A 500 ml-capacity autoclave was charged with 20 g (0.25 mole) of 1,3-cyclohexadiene, 79.3 g (1.17 moles) of cyclopexnten and 50 mg of hydroquinone. The reaction was conducted at 200° C, for 6 hours under agitation. The reaction mixture was cooled and hydroquinone was removed by filtration. Then, the unreacted cyclopentene was recovered and the residue was distilled under reduced pressure. A fraction boiling at 77° to 80° C under 8 mm Hg was collected. There was obtained 5.2 g (yield: 14wt.%) of endo-tricyclo[5.2.2.0$^{2,6}$]undec-8-ene.

Elementary Analysis Values: Found: C = 88.94%, H = 10.93% Calculated for $C_{11}H_{16}$: C = 89.12%, H = 10.88%.

Infrared Absorption Spectrum (neat, cm$^{-1}$): 3060, 2950, 2920, 2880, 1615, 1465, 1450, 1380, 1360, 1320, 1250, 1180, 1170, 970, 940, 915, 860, 845, 715

Mass Spectrum, m/e (relative intensity): 148 (M$^+$, 7), 120 (4), 92 (6), 91 (12), 81 (9), 80 (100), 79 (20), 78 (6), 77 (8), 67 (4), 51 (5), 41 (8), 39 (9)

NMR (CDCl$_3$ solvent, TMS internal standard, δ): 6.13 (multiplet, 2H, —HC =CH —), 0.7 - 2.75 (multiplet, 14H)

EXAMPLE 1

5 ml of tetrahydrofuran containing 2.84 g (20 millimoles) of BF$_3$.OET$_2$ was added dropwise over a period of 45 minutes to a suspension 0.57 g (15 millimoles) of sodium borohydride, 4.44 g (30 millimoles) of endo-tricyclo[5.2.2.0$^{2,6}$]undec-8-ene obtained in the Preparation and 15 ml of tetrahydrofuran under a nitrogen atmosphere, with agitation. After completion of the addition, the reaction mixture was further stirred for 3 hours at room temperature. The excess sodium borohydride was carefully decomposed with water, and 5 ml of a 3N aqueous solution of sodium hydroxide was added and then 5 ml of 30% aqueous hydrogen peroxide was slowly added dropwise. The reaction mixture was stirred at room temperature for 3 hours to oxidize the intermediate organic borane compound. After completion of the reaction, 50 ml of diethyl ether was added to the reaction mixture and the organic layer was separated. The aqueous layer was saturated with sodium chloride and extracted two times with diethyl ether. The extracts were combined with the organic layer, and the mixture was washed two times with a saturated aqueous solution of sodium chloride and dried over anhydrous sodium sulfate. When the solvent was distilled off under reduced pressure, 4.55 g (27.4 millimoles ) of crude 8-exohydroxy-endo-tricyclo [5.2.2.0$^{3,6}$]undecane was obtained (yield = 91 wt. %).

A pure product having a melting point of 66° to 67° C was obtained by fractional gas chromatography.

Elementary Analysis Values: Found: C = 79.18%, H = 11.07%; Calculated for $C_{11}H_{18}O$: C = 10.92%.

Infrared Absorption Spectrum (nujol, cm$^{-1}$): 3300 ($\nu$ O-H), 1065, 1015, 980, 910, 805

Mass Spectrum, m/e (relative intensity): 166 (M$^+$, 12), 148 (67), 122 (44), 93 (44), 81 (55), 80 (100), 79 (88), 78 (53), 67(61)

NMR (CDCL$_3$ solvent, TMS internal standard, $\delta$): 4.07 (multiplet, 1H, —C$\underline{H}$OH), 2.13 (singlet, 1H, OH), 2.4 -1.0 (multiplet, 16H)

EXAMPLE 2

Chick embryo fibroblasts were cultured for 2 to 3 days in a test tube according to the monolayer culture method and were inoculated with Newcastle disease virus of about 128 HAU (hemagglutination units). A culture medium of the stepwise dilution system containing a compound as listed below was added to the upper layer and the culturing was continued for 48 hours at 37° C. The antiviral effect was evaluated based on the hemagglutination reaction. The results obtained are shown below.

| Compound | Concentration ($\mu$g/ml) | %HAU* | CT** |
|---|---|---|---|
| 8-exo-hydroxy-endo- | 312 | 0.1 | + |
| tricyclo[5 . 2 . 2 . 0$^{2,6}$]- | 156 | 13 | ± |
| undecane | 78 | 100 | — |
| adamantylamine hydro- | 500 | below 1 | + |
| chloride | 250 | 9 | ± |
| | 125 | 100 | — |

Notes:

| Compound | Concentration ($\mu$g/ml) | %HAU* | CT** |
|---|---|---|---|

*: % HAU = $\dfrac{\text{HAU in sample containing test compound (dilution times inhibiting hemagglutination)}}{\text{HAU in untreated sample}} \times 100$

**: CT indicates the degree of the damage to chick embryo cells by the test compound.
— : no damage
± : small eruptions were formed on the cell surface
+ : cells of the monolayer parted from the tube wall
++ : cells were rounded or destroyed Thus, the formula (I) compound exhibits a more intense anti-viral activity than that of adamantylamine hydrochloride, a known useful anti-viral substance. The formula (I) compound can be used in the same way as adamantylamine hydrochloride, adjusting the dosage amounts as needed to reflect the more intense anti-viral activity of the formula (I) compound.

The embodiments of the invention in which an exclusive property or privilege is claimed are defined as follows:

1. A compound having the formula

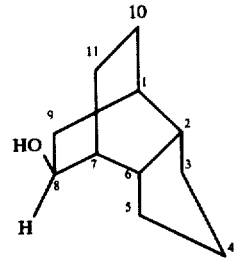

* * * * *